United States Patent [19]

McCartney et al.

[11] Patent Number: 4,647,149
[45] Date of Patent: Mar. 3, 1987

[54] ATTACHMENT OF OPTICAL FIBERS TO A CONNECTOR BODY

[75] Inventors: Ronald L. McCartney, Orange; Frank A. Marovich, Lake Forest, both of Calif.

[73] Assignee: American Hospital Supply Corporation, Evanston, Ill.

[21] Appl. No.: 546,492

[22] Filed: Oct. 28, 1983

[51] Int. Cl.⁴ .................................. G02B 6/36
[52] U.S. Cl. ................. 350/96.20; 350/96.26; 350/320
[58] Field of Search ............... 350/96.20, 96.21, 96.22, 350/96.26, 320

[56] References Cited
U.S. PATENT DOCUMENTS 3,690,769 9/1972 Mori ............................ 350/96.26 X
3,847,483 11/1974 Shaw et al. ................... 350/96.26 X
4,135,781 1/1979 Archer ........................... 350/96.20

FOREIGN PATENT DOCUMENTS 0020843 2/1977 Japan ................................ 350/96.21
0068809 4/1982 Japan ................................ 350/96.2
0102913 6/1983 Japan ................................ 350/96.2
0166311 10/1983 Japan ................................ 350/96.2

Primary Examiner—John Lee
Attorney, Agent, or Firm—Gordon L. Peterson

[57] ABSTRACT

An apparatus connectible to an instrument comprising an optical fiber for conducting light along its length and a connector body for use in coupling the optical fiber to the instrument. The connector body defines an enclosure having an entrance passage leading into the enclosure and an exit passage leading from the enclosure. The optical fiber extends through the entrance passage into the interior of the enclosure and into the exit passage. The optical fiber has an enlarged end portion which cooperates with the exit passage to retain the end portion in the exit passage.

16 Claims, 17 Drawing Figures

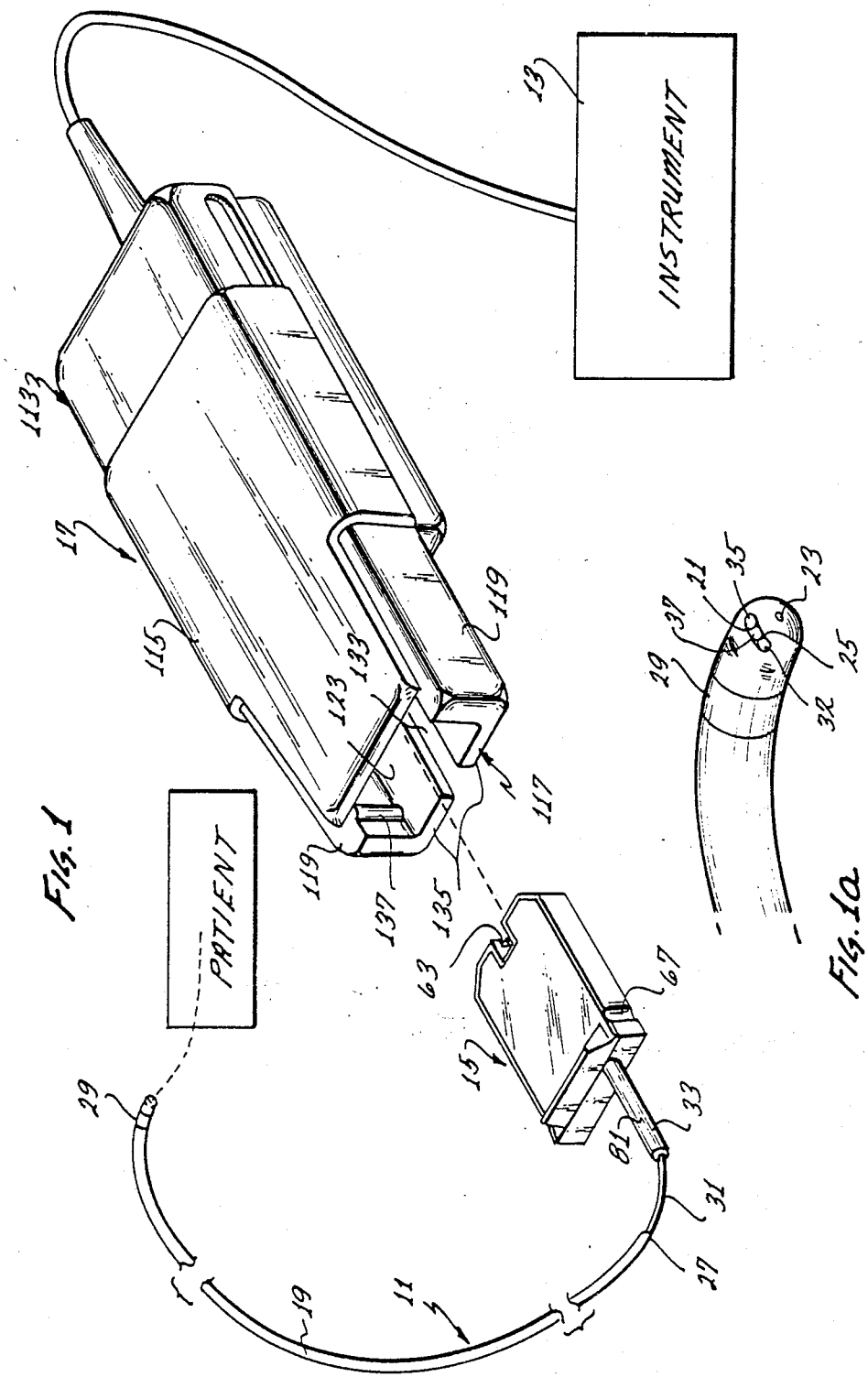

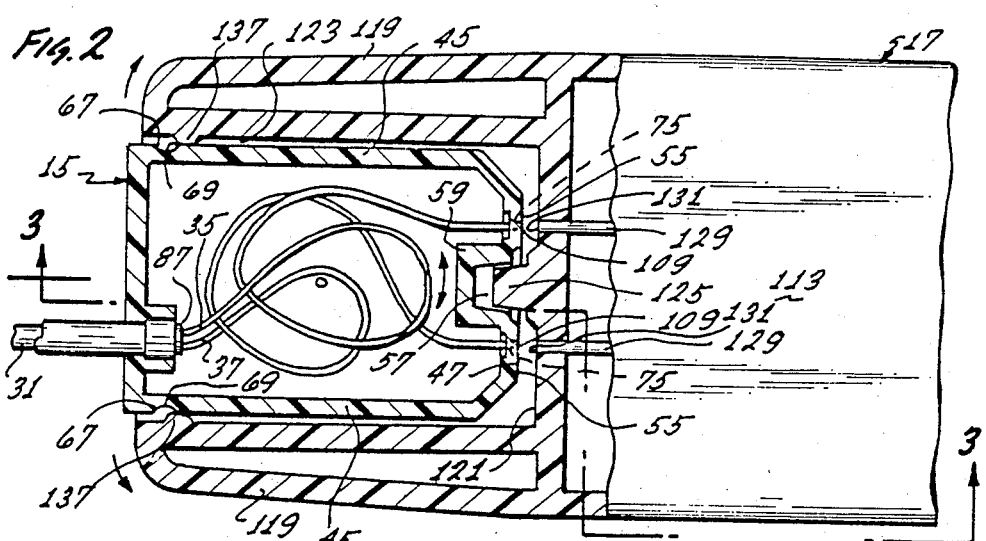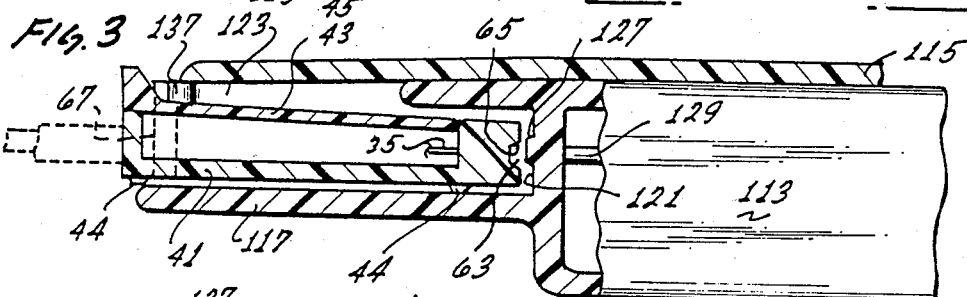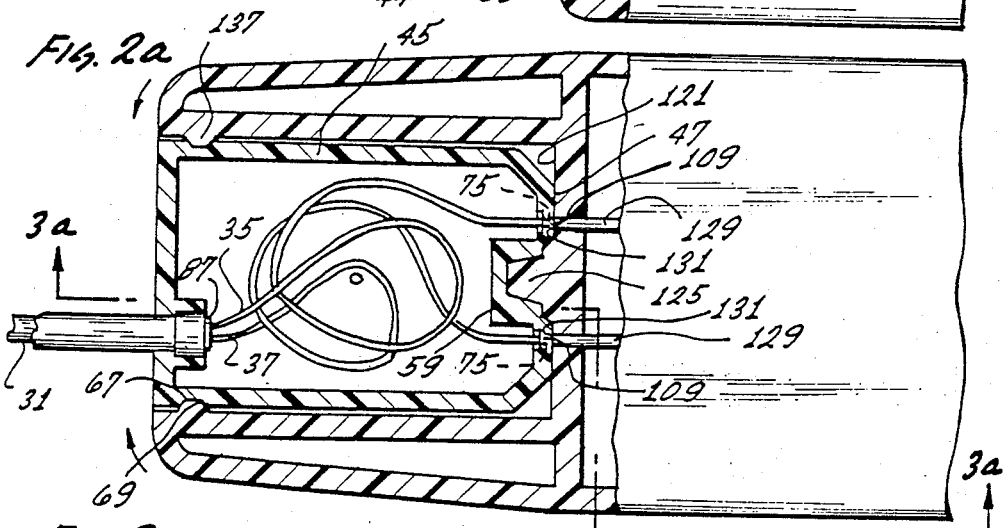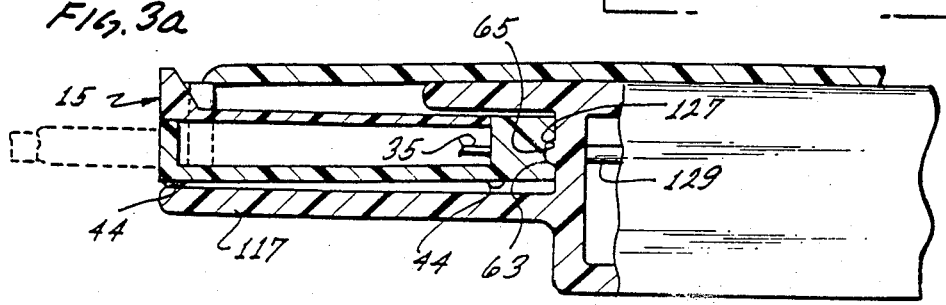

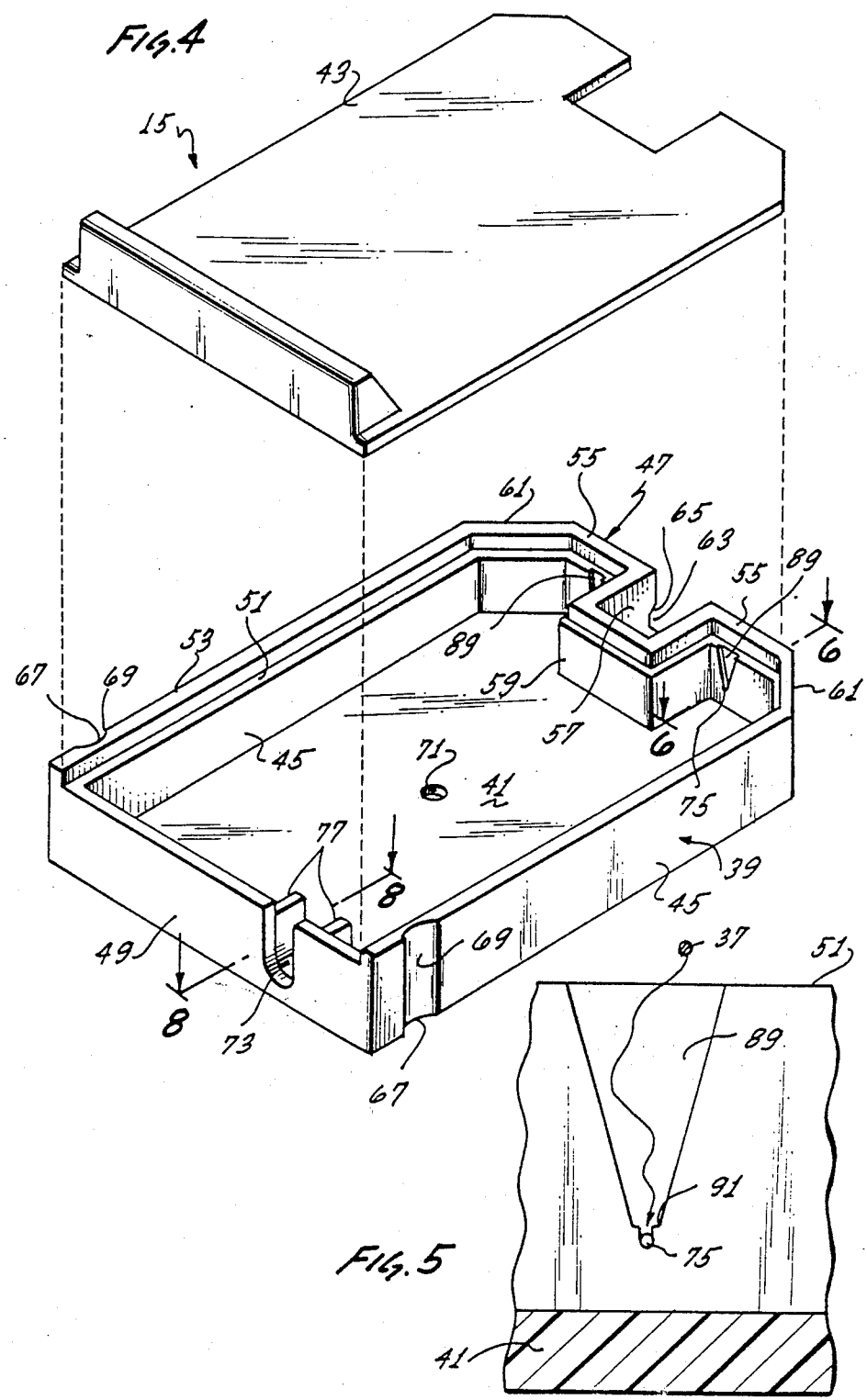

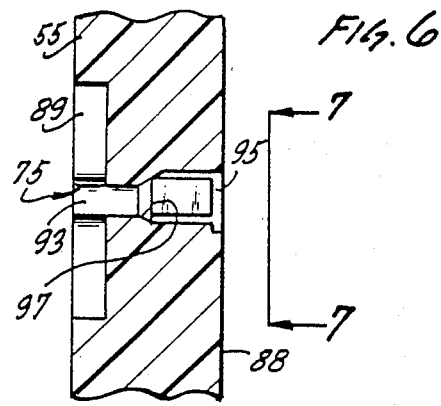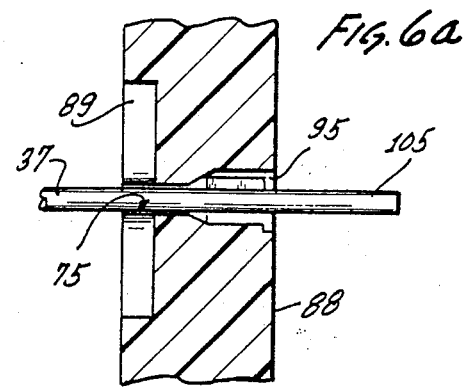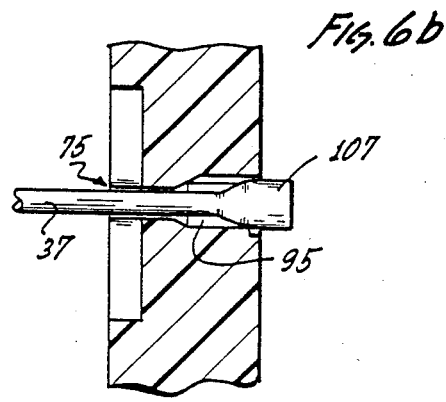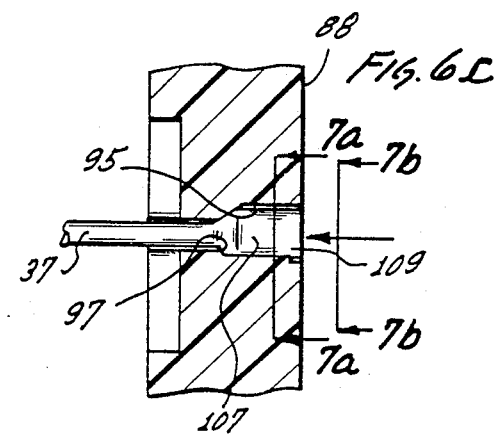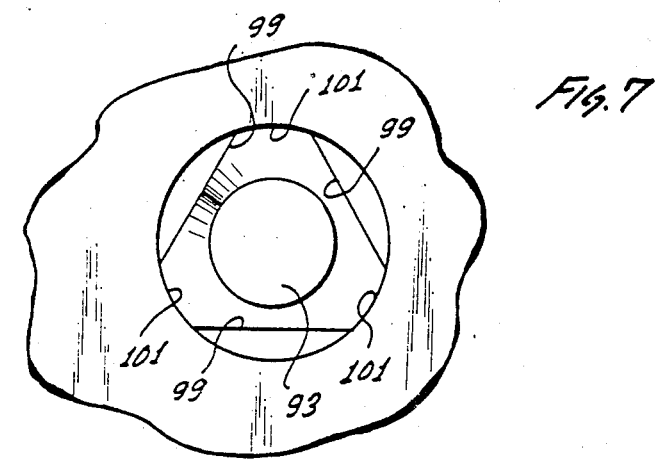

ATTACHMENT OF OPTICAL FIBERS TO A CONNECTOR BODY

BACKGROUND OF THE INVENTION

Fiber optics are used in catheters and probes for the purpose of transmitting light into and receiving light from internal regions of the body. Because a catheter or probe must be sized to be received within a vein or artery, the fiber optics used within such an apparatus must also be of very small diameter.

For example, a catheter or probe may include an elongated tube having proximal and distal openings and fiber optic means in the form of one or more fiber optic light conductors in the passage and extending through the proximal opening to provide a proximal section of the fiber optic means outside of the tube. The fiber optic means is coupled to a connector body, and the connector body is received within a cavity of a receptacle which optically couples the catheter to an instrument. The receptacle may be considered as part of the instrument. The instrument may, for example, provide a source of light for transmission through the catheter and the necessary equipment to process a light signal received from the catheter.

One problem with this construction is the mounting of the fine fiber optic light conductors on the connector body. The fiber optic light conductors, each of which comprises one or more optical fibers, must be located with respect to the connector body with great precision and securely retained in position. This is necessary so that light can be transmitted efficiently between the instrument and the catheter. Locating the fiber optic light conductor on the connector body with precision is difficult because of the small diameter of the optical fibers.

It is also important to assure that the connector body is tightly seated within the receptacle. If this is not done, losses will occur at the interface. Moreover, the connector body and receptacle must cooperate with each other to precisely position the connector body within the receptacle to maximize the optical coupling between the connector body and the receptacle.

SUMMARY OF THE INVENTION

This invention solves the problems noted above. With this invention, the fine, small diameter fiber optic light conductors are securely and precisely mounted on the connector body. This is accomplished in a way which facilitates assembly and minimizes production cost. Although these features are particularly applicable to a catheter or probe which is sized to be received with a vein or artery, they are also applicable to the mounting of a fiber optic light conductor on a connector body for use with various other devices.

The connector body of this invention can advantageously include wall means defining an enclosure and an entrance passage and an exit passage in the wall means. The fiber optic means extends through the entrance passage into the enclosure and into the exit passage. The fiber optic means has a proximal end within or closely adjacent the exit passage. Because the exit passage can be precisely located, the end of the fiber optic means is correspondingly accurately located and it can be optically coupled to a selected part of the receptacle.

The fiber optic means is retained in the exit passage. With this invention, the retaining means includes a shoulder in the exit passage and an enlargement on the fiber optic means adjacent the proximal end thereof which cooperates with the shoulder to at least assist in retaining the fiber optic means in the exit passage. An adhesive may also be used.

The fiber optic means is preferably of the type which can be radially enlarged by heating. This permits the enlargement to be formed by the application of heat.

To facilitate insertion of the end of the fiber optic means into the exit passage, a tapered groove is provided in the wall of the enclosure which leads to, and narrows toward, the exit passage. To prevent the entrance of ambient light into the enclosure at this region, the tapered groove preferably does not extend completely through the wall.

More specifically, the exit passage has an entrance section on one side of the shoulder and an exit section on the other side of the shoulder, and the exit section has first and second surface portions. The enlargement is radially, compressively engaged by the first surface portion, and material is displaced from at least one of the first surface portion and the enlargement to the region between the second surface portion and the enlargement. Preferably, material from the enlargement is displaced. Thus, the first surface portion provides for the compressive engagement and the second surface portion allows for the displacement of material resulting from the compressive engagement. The compressive engagement tightly retains the end portion of the fiber optic means within the exit passage so that any adhesive being used can cure, and there is no need for a separate fixture to hold these components in position during curing of the adhesive. Preferably, the first surface portion includes at least three generally flat surfaces arranged circumferentially within the exit passage. Although curved surfaces could be used, they tend to present sharp corners for the enlargement, and for that reason, curved surfaces are not preferred. In a preferred construction, the flat surfaces are set back from the exterior opening of the exit passage so that, in molding the connector body, there will be no flash at the exterior opening.

The fiber optic means may include one or more fiber optic light conductors, and one of the exit passages is provided for each of the fiber optic light conductors. Each of the fiber optic light conductors may include one or more optical fibers. The fiber optic light conductors may form a portion of a probe or catheter.

In carrying out the method of this invention, a fiber optic light conductor is inserted through the exit passage so that it has an end portion on the exit side of the passage. The end portion of the fiber optic light conductor is then radially enlarged, and this is preferably carried out by heating as described above. The radially enlarged end portion is then forced back into the exit section of the passage to compressively engage the enlarged end portion with the first surface portion and to displace material from one or both of the first surface portion of the wall and the enlarged end portion as described above.

The invention, together with additional features and advantages thereof, may best be understood by reference to the following description taken in connection with the accompanying illustrative drawing.

BRIEF DESCRIPTION OF THE DRAWING

FIG. 1 is a partially schematic, isometric view illustrating an apparatus constructed in accordance with the teachings of this invention.

FIG. 1a is a fragmentary, isometric view of a distal end portion of a catheter.

FIGS. 2 and 2a are fragmentary, top plan views of the receptacle and connector body, with the connector body partially and fully inserted into the receptacle, respectively.

FIGS. 3 and 3a are fragmentary sectional views taken along lines 3—3 and 3a—3a of FIGS. 2 and 2a, respectively.

FIG. 4 is an exploded isometric view of the connector body with the light conductors removed.

FIG. 5 is an enlarged, fragmentary sectional view of a portion of the connector body which includes the exit passage.

FIG. 6 is an enlarged, fragmentary sectional view taken generally along line 6—6 of FIG. 4.

FIGS. 6a-6c are fragmentary, sectional views similar to FIG. 6 illustrating a preferred method of retaining the light conductor in the exit passage.

FIG. 7 is an enlarged elevational view taken generally along line 7—7 of FIG. 6.

DESCRIPTION OF THE PREFERRED EMBODIMENT

Figure 7A:
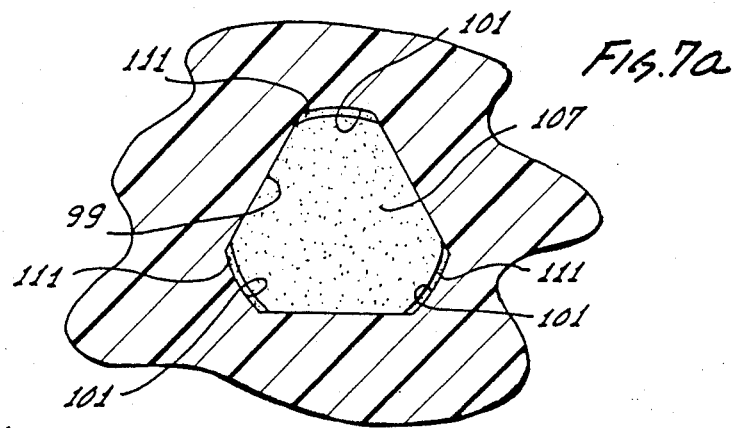
FIGS. 7a and 7b are views taken generally along lines 7a—7a and 7b—7b, respectively, of FIG. 6c.

FIG. 1 shows a catheter 11 which can be releasably coupled to an instrument 13 using a connector body 15 and a receptacle 17. The receptacle 17 may be considered as part of the instrument 13. Although the features of this invention are particularly adapted for use with a catheter, the invention is not limited to use with a catheter, and the particular catheter shown is purely illustrative.

The catheter 11 includes a tube 19 sized to be received within a vein or an artery of a patient and having proximal and distal ends and a plurality of lumens or passages, including passages 21 and 23 extending longitudinally through it. The passage 21 has a distal opening 25 (FIG. 1a) and a proximal opening 27 (FIG. 1). A balloon 29 is provided on the tube 19 adjacent the distal tip of the catheter.

The catheter 11 also includes fiber optic means 31 extending completely through the passage 21 of the tube 19 from the distal opening 25 through the proximal opening 27 to provide a proximal section 33 of the fiber optic means outside of the tube. Of course, other tubing in communication with the other passages of the tube 19 can also exit at the proximal opening 27. Although various constructions are possible, in the embodiment illustrated, the fiber optic means 31 includes fiber optic light conductors 35 and 37 for conducting light to the distal opening 25 and for conducting a light signal away from the distal opening 25, respectively. The distal ends of the light conductors are tightly retained within the passage 21, which is of larger cross section than the two light conductors, by a spacer 32 (FIG. 1a). A catheter of this type can be used to measure the oxygen saturation of blood by determining its color absorption characteristics in accordance with known techniques. To make this determination, the catheter 11 is inserted into the heart of the patient to place the distal opening 25 in the pulmonary artery.

The proximal section 33 of the fiber optic means 31 is coupled to the connector body 15, and the details of the connector body are shown in FIGS. 2-8a. The connector body 15 has wall means which define an enclosure, and the wall means includes a circumscribing peripheral wall 39, a floor 41 and a cover 43 (FIG. 4). Supporting feet 44 (FIGS. 3 and 3a) extend downwardly from the floor 41. The peripheral wall 39 includes opposed side walls 45 an end wall or face 47 and an end wall 49. The peripheral wall 39 extends perpendicular to the floor 41 and has a ledge 51 and a lip 53 projecting from the ledge. The cover 43 is receivable within the lip 53 and onto the ledge 51 with a snap fit to releasably retain the cover in position.

The face 47 includes identical face sections 55 (FIGS. 2 and 4) separated by a tapered gap 57 which narrows as it extends inwardly of the enclosure and which is defined by a channel section 59. The face 47 also has inclined corner sections 61 which join the sections 55 to the side walls 45, respectively.

The face sections 55 have identical recesses 63, respectively, which open into the gap 57 (FIGS. 3, 3a and 4). The face sections 55 are flat and coplanar, except for the recesses 63. Each of the recesses 63 is partially defined by an inclined cam follower surface 65. The other side surfaces of each of the recesses 63 are also inclined and they terminate inwardly in a flat bottom surface.

Each of the side walls 45 has a recess or groove 67 in its exterior surface, and each of the grooves has a longitudinal axis which extends perpendicular to the longitudinal axis of the associated side wall. Each of the grooves 67 is identical and is partially defined by a inclined cam surface 69 along the forward or leading side of the groove. The cam surfaces 69 are used as described more fully hereinbelow for connecting the connector body 15 to the receptacle 17.

The connector body 15 can be of two-piece, molded plastic construction as shown in FIG. 4. The cover 43 is configured to mate with and close the opening at the upper end of the construction formed by the peripheral wall 39 and the floor 41. The floor 41 may have a central aperture 71.

Figure 8:
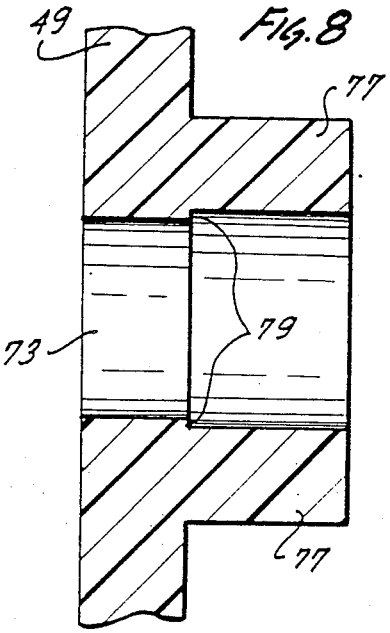
FIGS. 8 and 8a are enlarged fragmentary sectional views taken generally along line 8—8 of FIG. 4 and illustrating the entrance passage empty and with the light conductors installed therein, respectively.

The end wall 49 has an entrance passage 73, and each of the face sections 55 has an identical exit passage 75. Because the exit passages 75 are identical, only one of them is described in detail herein. As shown in FIG. 8, the end wall 49 has a pair of legs 77 which project inwardly into the enclosure and define shoulders 79 on opposite sides of the entrance passage 73.

Figure 8A:
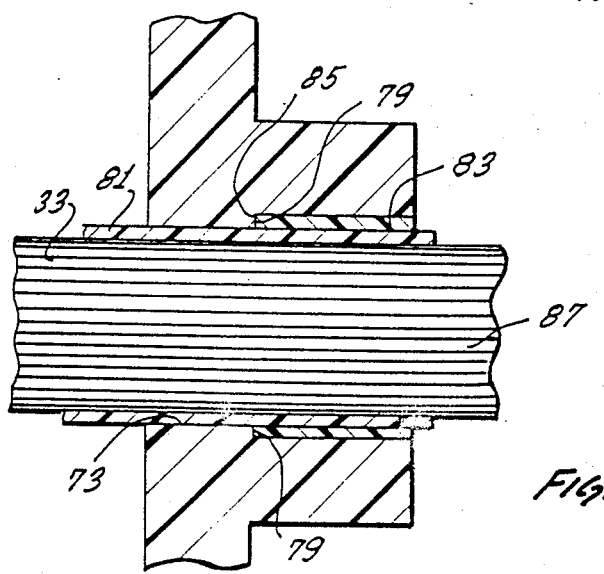

The entrance passage 73 cooperates with the proximal section 33 of the fiber optic means 31 as shown in FIG. 8a. Specifically, the proximal section 33 includes a sheet of shrink tubing 81 and a shorter section of shrink tubing 83 shrunk over and glued to the tubing 81. The tubing 83 forms an annular shoulder 85 which engages the shoulders 79 as shown to provide strain relief.

Thus, the proximal section 33 of the fiber optic means 31 passes through the entrance passage 73 and into the interior of the enclosure. As shown in FIGS. 2 and 2a, the light conductors 35 and 37 extend beyond the end of a sheath 87 in which they are encased, and an excess length of both of the light conductors is provided within the enclosure. In this embodiment, each of the light conductors 35 and 37 is in the form of a fine, small diameter optical fiber. The light conductors 35 and 37 extend into the exit passages 75, respectively, and they are retained in these exit passages with their ends flush with the outer surface 88 (FIG. 6c) of the associated face sections 55.

To facilitate insertion of the light conductors 35 and 37 into the associated exit passage 75, tapered lead-in grooves 89 are provided on the interior surfaces of the face sections 55 as shown in FIGS. 4 and 5. Each of the lead-in grooves 89 is identical and extends from the ledge 51 to the associated exit passage 75, and it progressively narrows as it extends toward such exit passage. In the embodiment illustrated, each of the lead-in grooves 89 tapers linearly, except for a step 91 closely adjacent the exit passage 75. With this construction, the light conductor 37 can be easily inserted into the wide end of the lead-in groove 89 adjacent the ledge 51 and guided toward, and into, the exit passage 75.

A preferred construction of the exit passage 75 is shown in FIGS. 6 and 7. The exit passage 75 has an entrance section 93 of reduced cross section, an exit section 95 of enlarged cross section, a shoulder 97 between these sections, and flat surfaces or surface portions 99 and curved surfaces or surface portions 101 arranged circumferentially in the exit section of the passage. The flat surfaces 99 are set back slightly from the exterior surface 88 of the face section 55 at which the exit passage 75 opens. If desired, a region of the flat surfaces 99 adjacent to the outer surface 88 may be inclined radially inwardly as they extend toward the outer surface 88.

The surfaces 99 and 101 are arranged circumferentially in the exit section 95. Although various constructions are possible, in the embodiment illustrated, there are three identical flat surfaces 99 and they are spaced apart 120 degrees. Each of the curved surfaces 101 is identical and comprises a segment of a cylinder. One of the curved surfaces 101 lies circumferentially between adjacent flat surfaces 99.

The flat surfaces 99 are closer together radially than the surfaces 101. For example, the flat surfaces 99 may be sized and arranged to receive a member of 0.0135 inch diameter, and the curved surfaces 101 may be segments of a cylinder having a diameter of 0.016 inch.

To attach the light conductor 37 to the face section 55, the light conductor 37 is inserted into the exit passage 75 using the lead-in groove 89 and through the exit passage as shown in FIG. 6a. Accordingly, the light conductor 37 has an end portion 105 on the exit section side of the exit passage 75. Next, the end portion 105 is radially enlarged. Although the radial enlarging of the light conductor 37 can be carried out in different ways, this is preferably accomplished by using a light conductor of the type which radially enlarges in response to being heated. For example, an optical fiber comprising an acrylic core and a fluoropolymer sheath will radially expand and axially contract in response to heating. Preferably, the end portion 105 is heated to radially enlarge the end portion to form an enlargement 107 (FIG. 6b) of the desired cross-sectional area which may be frusto-conical with the major diameter at the end of the light conductor. For example, a light conductor having a diameter of 0.010 inch can be enlarged to a diameter of about 0.015 inch by exposing the end portion 105 to a temperature of about 550 degrees Fahrenheit and continuing that exposure for about 8 seconds.

Figure 7B:
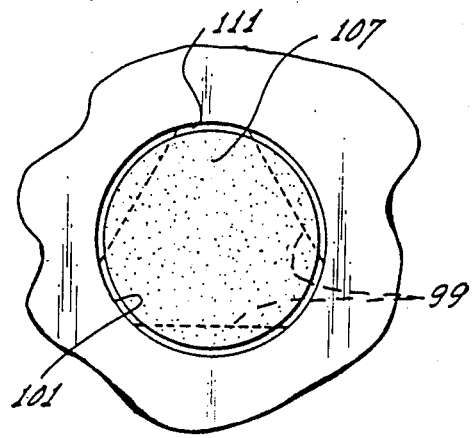

Next, the enlargement 107 is forced into the exit section 95 of the exit passage 75 to compressively engage the enlargement with the flat surfaces 99 as shown in FIGS. 6c, 7a and 7b. Preferably, the enlargement 107 is pushed back into the exit section 95. As shown in FIG. 6c, at the completion of this step, a proximal end 109 of the light conductor 37 is flush with the outer surface 88 and is therefor at a known location on the surface 88.

The enlargement 107 is somewhat deformable and its diameter is greater than the diameter than can be accepted by the flat surfaces 99. Accordingly, the forcing of the enlargement 107 between the flat surfaces 99 displaces material from the enlargement 107 circumferentially to regions 111 (FIG. 7a) between the enlargement 107 and the curved surfaces 101. As shown in FIG. 7a, there are three regions 111, each of which is in the form of a radial gap. Accordingly, the enlargement 107 is frictionally retained in the exit section 95 by the flat surfaces 99 and, in addition, the enlargement 107 at its juncture with the non-enlarged portion of the light conductor 37 defines a shoulder which engages the shoulder 97 to inhibit withdrawal of the light conductor through the entrance section 93. Preferably, a suitable adhesive is applied to the enlargement 107 and/or to the surfaces of the exit passage 75 prior to forcing the enlargement 107 back into the exit section 95. Accordingly, the frictional retention of the enlargement 107 by the flat surfaces 99 serves, in effect, as a fixture to hold the light conductor 37 within the exit passage 75 while the adhesive cures. Inclining regions of the flat surfaces 99 adjacent the outer surface 88 radially inwardly as they extend toward the surface 88 helps to lock the enlargement 107 in the exit passage 75. The flat surfaces 99 also accurately center the light conductors.

The receptacle 17 (FIGS. 1–3a) comprises a body 113 and a cover 115 mounted on the body for slidable movement longitudinally of the body. The body 113, which may be molded from a suitable plastic material, comprises a floor 117, side walls 119 and a face 121 (FIGS. 2–3) cooperating to define a cavity 123 sized to receive the connector body 15. The face 121 is flat and planar, except for a central wedge-shaped projection 125 adapted to be received within the gap 57 and for cam surfaces 127 adapted to cooperate with the cam follower surfaces 65, respectively. Light conductors 129 extend within the receptacle 17 and have their ends mounted in and flush with the face 121 at locations 131, respectively. The locations 131 are arranged to be in confronting and substantially aligned relationship with the exit passages 75, respectively, when the connector body 15 is received within the cavity 123.

The floor 117 has a slot 133 to separate the adjacent portions of the receptacle 17 into resilient sections 135 (FIG. 1). A projection 137 is mounted on and carried by each of the side walls 119. The resilient sections 135 and the projections 137 form biasing means or a biasing member capable of exerting inward force on the connector body 15. Of course, the biasing means can be formed in other ways.

To attach the connector body 15 to the receptacle 17, the connector body is advanced into the cavity 123 and slid in a direction to bring the faces 47 and 121 closer together. During this sliding movement, the feet 44 of the connector body 15 slide along the floor 117 of the receptacle 17, and the inner surfaces of the side walls 119, the floor 117, the projection 125 and the confronting surfaces of the connector body 15 form guide means for guiding the connector body along a path in the cavity 123 to place the faces 47 and 121 in confronting relationship and to bring the proximal ends 109 of the light conductors 35 and 37 into engagement with the locations 131. As the connector body 15 is advanced into the cavity 123, the side walls 45 of the connector body 15 engage the projections 137 and urge the resilient sections 135 resiliently away from each other. When the proximal ends 109 are nearly in engagement with the locations 131 as shown in FIGS. 2 and 3, the projections 137 engage the cam surfaces 69 and urge the connector body 15 farther into the cavity 123 to place the faces 47 and 121 into engagement and to place the proximal ends 109 into engagement and substantial axial alignment with the locations 131. The projections 137 cooperate with the groove 67 to retain the connector body 15 in the cavity 123 of the receptacle 17.

In the position shown in FIGS. 2 and 3, the cam follower surfaces 65 are nearly in engagement with the cam surfaces 127. The final advancing motion of the connector body 15 into the cavity 123 causes the cam follower surfaces 65 to engage the cam surfaces 127 to lift the forward end of the connector body 15, and in particular the forward foot 44, off of the floor 117 as shown in FIG. 3a. This elevation of the forward end of the connector body 15 accurately positions the exit passages 75 and brings them into correct alignment with the locations 131. The cam surfaces 127 and the cam follower surfaces 65 also cooperate to assist in holding the connector body 15 in the desired orientation within the cavity 123.

The cam surfaces 127 and the cam follower surfaces 65 form a portion of the guiding means for guiding the connector body 15 into the proper location within the cavity 123. Thus, the path along which the connector body 15 moves extends in a first direction, which is generally along the longitudinal axis of the body 113, until the cam follower surfaces 65 contact the cam surfaces 127 and then in a second direction along the cam surfaces 127. This latter portion of movement of the connector body 15 occurs when the faces 47 and 121 are closely adjacent and may be under the influence of the biasing action of the receptacle 17 and the cooperation between the projections 137 and the cam surfaces 69.

The cooperation between the projections 137 and the cam surfaces 69 automatically draws the connector body 15 completely into the correct seated position within the cavity 123. This final movement is accompanied by an audible "click" to inform the operator of the correct seating. The force provided assures that the optical portions, i.e., the proximal ends 109 and the locations 131, will be in contact and in proper registry.

In use, the instrument 13 may provide light through one of the light conductors 129 to the light conductor 35, and this light is transmitted through the interface at the faces 47 and 121 to the light conductor 35 which transmits it to the distal opening 25. Assuming that the catheter 11 is correctly positioned within a vein or artery within the patient, the light at the distal opening from the light conductor 35 is directed against the patient's blood. The blood reflects light into the light conductor 37, and the reflected light forms a signal having a characteristic related to the absorption characteristics of the blood. The light signal is transmitted through the light conductor 37 and into the other of the light conductors 129. The light signal is converted to an electrical signal within the receptacle 17 and transmitted to the instrument 13 for processing in accordance with known techniques to determine the oxygen saturation of the blood.

Although an exemplary embodiment of the invention has been shown and described, many changes, modifications and substitutions may be made by one having ordinary skill in the art without necessarily departing from the spirit and scope of this invention.

We claim:

1. An apparatus connectible to an instrument, said apparatus comprising:
   fiber optic means for conducting light along its length;
   a connector body for use in coupling the fiber optic means to the instrument;
   said connector body including wall means defining an enclosure and an entrance passage and an exit passage in the wall means, the fiber optic means extending through the entrance passage into the enclosure and into the exit passage, said fiber optic means having a proximal end within or closely adjacent the exit passage whereby said proximal end of the fiber optic means can be optically coupled to a selected part of the instrument;
   means for retaining the fiber optic means in said exit passage;
   said retaining means including a shoulder in said exit passage and an enlargement on said fiber optic means adjacent the proximal end thereof which cooperates with said shoulder to at least assist in retaining the fiber optic means in said exit passage; and
   said exit passage having an entrance section on one side of said shoulder and an exit section extending beyond said shoulder on the other side of said shoulder and the exit section having first and second surface portions, said enlargement being radially compressively engaged by the first surface portion and material being displaced from at least one of the first surface portion and the enlargement to the region between the second surface portion and the enlargement.

2. An apparatus as defined in claim 1 wherein said fiber optic means can be radially enlarged by heating and said enlargement includes a portion of the fiber optic means enlarged by heating.

3. An apparatus as defined in claim 1 wherein the enlargement is spaced radially from the second surface portion and said first and second surface portions are circumferentially arranged.

4. An apparatus as defined in claim 1 wherein said first surface portion includes at least three generally flat surfaces arranged circumferentially within said exit passage.

5. An apparatus as defined in claim 4 wherein said exit passage opens at the exterior of said enclosure and said flat surfaces are set back from said exterior opening of the exit passage, said fiber optic means can be radially enlarged by heating and said enlargement includes a portion of the fiber optic means enlarged by heating.

6. An apparatus as defined in claim 4 wherein the exit passage has an outlet and a region of each of said flat surfaces adjacent the outlet is inclined radially inwardly as it extends toward the outlet of the exit passage.

7. An apparatus as defined in claim 1 including a tapered groove in said wall means and within said enclosure leading to and narrowing toward the exit passage to facilitate insertion of the fiber optic means into said exit passage, said groove extending generally transversely of the exit passage.

8. An apparatus as defined in claim 1 including an elongated tube sized to be received within a vein or artery and having proximal and distal ends and at least one elongated passage with proximal and distal openings, said fiber optic means being partially in said passage and being capable of conducting light to said distal opening and from said distal opening, said fiber optic means extending through said proximal opening to provide a proximal section of said fiber optic means outside of said tube, at least a portion of the proximal section extending through said entrance passage and into said enclosure.

9. An apparatus as defined in claim 8 wherein said fiber optic means includes first and second fiber optic light conductors, said exit passage is a first exit passage and said enclosure has a second exit passage, and said second fiber optic light conductor is received in said second exit passage.

10. A method of installing a fiber optic light conductor in a passage through a wall, said method comprising:
providing a passage with an entrance section of reduced cross section, an exit section of enlarged cross section, a shoulder between said entrance and said exit sections, and first and second surface portions arranged circumferentially in the exit section of the passage;
inserting the fiber optic light conductor through the passage so that the fiber optic light conductor has an end portion on the exit section side of the passage;
radially enlarging the end portion of the fiber optic light conductor; and
forcing the radially enlarged end portion into the exit section of the passage to compressively engage the enlarged end portion with the first surface portion and to displace some material from at least one of the first surface portion and the enlarged end portion circumferentially to the region between the second surface portion and the enlarged end portion and to bring the enlarged end portion into proximity to the shoulder whereby the end portion is frictionally retained in the exit passage and the enlarged end portion can inhibit withdrawal of the fiber optic light conductor through the entrance section of the passage.

11. A method as defined in claim 10 wherein the wall has a tapered groove on the entrance section side thereof leading to and narrowing toward the entrance section and said step of inserting includes passing the end portion of the fiber optic light conductor through at least a portion of the tapered groove and into the entrance section of the passage.

12. A method as defined in claim 10 wherein the fiber optic light conductor is of the type which radially expands when heated and said step of radially enlarging includes heating the end portion of the fiber optic light conductor to radially enlarge the end portion to the extent desired.

13. A method as defined in claim 10 wherein the enlarged end portion is at least somewhat deformable and is radially compressively loaded by said first surface portion to displace some of the material thereof to the region between the second surface portion and the enlarged end portion.

14. A method as defined in claim 10 wherein said step of providing includes providing a passage in which the first surface portion comprises at least three generally flat surfaces arranged at approximately 120 degrees with respect to each other and with the second surface portion comprising three surfaces located circumferentially between adjacent flat surfaces.

15. A method as defined in claim 10 wherein said end portion terminates in an end, said wall has a surface on and contiguous the exit section side of the passage and said step of forcing includes pushing the fiber optic light conductor into said exit section until said end of the fiber optic light conductor is substantially flush with said surface of the wall.

16. A method as defined in claim 10 including applying an adhesive to at least one of the enlarged end portion and the surface of the exit section and using the frictional retention of the enlarged end portion in the exit section as a fixture to hold the enlarged end portion in the exit section while the adhesive cures.

* * * * *